(12) United States Patent
Goedje et al.

(10) Patent No.: US 7,850,617 B2
(45) Date of Patent: Dec. 14, 2010

(54) PATIENT MONITORING APPARATUS AND METHOD FOR DETERMINING VOLUME RESPONSIVENESS OF A MONITORED PATIENT

(75) Inventors: Oliver Goedje, Deining (DE); Manu Malbrain, Lovenjoel (BE); Stephan Joeken, Schopfheim (DE); Matthias Bohn, Munich (DE)

(73) Assignee: Pulsion Medical Systems AG, Munich (DE)

( * ) Notice: Subject to any disclaimer, the term of this patent is extended or adjusted under 35 U.S.C. 154(b) by 743 days.

(21) Appl. No.: 11/784,003

(22) Filed: Apr. 5, 2007

(65) Prior Publication Data

US 2007/0287929 A1    Dec. 13, 2007

(30) Foreign Application Priority Data

Apr. 19, 2006    (EP)    ................... 06112767

(51) Int. Cl.
A61B 5/02    (2006.01)
(52) U.S. Cl. .................. 600/526; 600/300; 600/309; 600/508; 600/507
(58) Field of Classification Search .............. 600/526, 600/309, 300, 481, 508, 507
See application file for complete search history.

(56) References Cited

U.S. PATENT DOCUMENTS

| 5,383,468 | A | 1/1995 | Nakayama et al. |
| 5,526,817 | A * | 6/1996 | Pfeiffer et al. ............. 600/504 |
| 6,315,735 | B1 | 11/2001 | Joeken et al. |
| 6,537,230 | B1 | 3/2003 | Pfeiffer et al. |
| 7,314,449 | B2 | 1/2008 | Pfeiffer et al. |
| 7,588,542 | B2 | 9/2009 | Pfeiffer et al. |
| 7,666,146 | B2 | 2/2010 | Pfeiffer et al. |

FOREIGN PATENT DOCUMENTS

| EP | 1 034 737 A1 | 9/2000 |
| EP | 1 236 435 A1 | 9/2002 |
| JP | SHO 64-070024 | 3/1989 |
| JP | PCT HEI 09-500029 | 1/1999 |

(Continued)

OTHER PUBLICATIONS

Marik, Paul, MD., "Assessment of intravascular volume: A comedy of errors," Crit. Care Med 2001, vol. 29, No. 8, pp. 1635-1636, (Spec, p. 2).

(Continued)

*Primary Examiner*—Robert L Nasser
*Assistant Examiner*—Michael D'Angelo
(74) *Attorney, Agent, or Firm*—Collard & Roe, P.C.

(57) ABSTRACT

From the global end-diastolic volume GEDV and the global ejection fraction GEF the patient monitor (4) determines a corrected global end-diastolic volume cGEDV according to $$cGEDV = GEDV / f(GEF)$$

Figure 1:
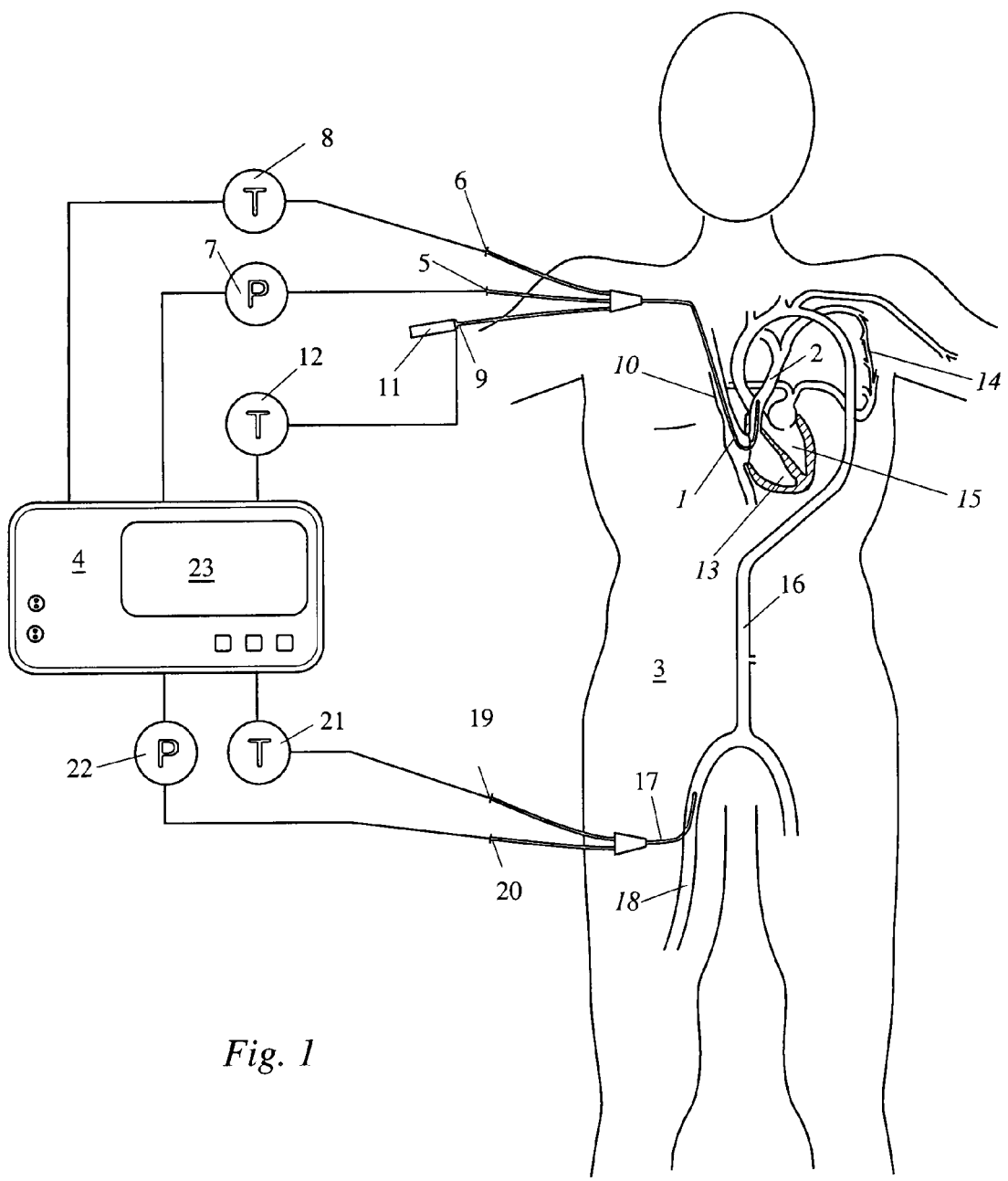

which is used as a novel parameter for volume responsiveness of the patient (3). In the above formula, f(GEF) is a correction function depending on global ejection fraction GEF. Further, from the right ventricular end-diastolic volume RVEDV and the right ventricular ejection fraction RVEF the patient monitor (4) determines a corrected right ventricular end-diastolic volume cRVEDV according to $$cRVEDV = RVEDV1 f(RVEF)$$

which is used as another novel parameter for volume responsiveness of the patient (3). In the above formula, f(RVEF) is a correction function depending on right ventricular ejection fraction RVEF.

35 Claims, 2 Drawing Sheets

FOREIGN PATENT DOCUMENTS

| JP | PCT 2003-512120 | 4/2003 |
|---|---|---|
| JP | HEI 04-166130 | 6/2004 |
| JP | 2004-202250 | 7/2004 |
| JP | 2005-305173 | 11/2005 |
| JP | 2005-329237 | 12/2005 |

OTHER PUBLICATIONS

Michard, F. and Teboul, J., "Predicting Fluid Responsiveness in ICE Patients: A Critical Analysis of the Evidence," Crit. Care Review, vol. 121, No. 6, 2002, pp. 2000-2008, (Spec, p. 2).

Kumar, A. et al., "Pulmonary artery occlusion pressure and central venous pressure fail to predict ventricular filling volume, cardiac performance, or the response to volume infusion in normal subjects," Crit. Care Med. 2004, vol. 32, No. 3, pp. 691-699, (Spec, p. 2).

Tousignant, C. et al., "The Use of Transesophageal Echocardiography for Preload Assessment in Critically ill Patients," Critical Care and Trauma, 2000, International Anesthesia Research Society, vol. 90, pp. 351-355, (Spec, p. 2).

Diebel, L. et al., "End-Diastolic Volume: A Better Indicator of Preload in the Critically ill," Arch Surg. vol. 127, 1992, pp. 817-822, (Spec, p. 2).

Michard, F., and Reuter, D., "Assessing cardiac preload or fluid responsiveness? It depends on the question we want to answer," Intensive Care Med, 2003, vol. 29, p. 1396, (Spec, p. 2).

Michard, F. et al., "Relation between Respiratory Changes in Arterial Pulse Pressure and Fluid Responsiveness in Septic Patients with Acute Circulatory Failure," Am. J. Respir. Crit. Care Med, 2000, vol. 162, pp. 134-138, (Spec, p. 2).

Marx, G. et al., "Assessing fluid responsiveness by stroke volume variation in mechanically ventilated patients with severe sepsis," European Journal of Anesthesiology, 2004, vol. 21, pp. 132-138, (Spec, p. 2).

Hofer, C. K., et al., "Stroke Volume and Pulse Pressure Variation for Prediction of Fluid Responsiveness in Patients . . . ," The Cardiopulmonary and Critical Care Journal, American College of Chest Physicians, 2005, vol. 128, pp. 848-854, (Spec, pp. 2-3).

* cited by examiner

PATIENT MONITORING APPARATUS AND METHOD FOR DETERMINING VOLUME RESPONSIVENESS OF A MONITORED PATIENT

The present invention relates to patient monitoring apparatus, in particular to patient monitoring apparatus for determining volume responsiveness of a monitored patient. Further, the present invention also relates to a method for determining volume responsiveness of a monitored patient.

Patient monitoring apparatus are commonly used in modern day hospitals for monitoring the condition of the circulatory system of critically ill patients. As is well known to the person skilled in the art, patient monitoring apparatus may function according to one of a variety of measurement and evaluation principles, such as (right heart or transpulmonary) thermodilution, dye dilution and pulse contour analysis, or may combine two or more of these measurement and evaluation principles. Applying suitable methods according to these principles yields a variety of parameters which enable the physician in charge to judge the present condition of the patient and to take appropriate counter measures, if the condition should worsen. Particularly important among these parameters are cardiac output CO and global end-diastolic volume GEDV. Other important parameters include extravascular lung water EVLW, pulse pressure variation PPV, stroke volume variation SSV and systemic vascular resistance SVR.

Patient monitoring apparatus for determining one or more of the above parameters are described inter alii in U.S. Pat. No. 5,526,817, U.S. Pat. No. 6,315,735 and U.S. Pat. No. 6,537,230.

A particularly critical condition of the circulatory system, which is referred to by the term shock, is an imbalance between circulatory energy (the product of pressure and volume) and peripheral demand. If an intervention to reverse this imbalance is to have any chance of success, the mode of failure of the circulatory system needs to be ascertained. Optimal hemodynamic monitoring should be able to provide an answer to the question whether a state of shock is caused by an unusually high peripheral demand, or whether the energy output of the pressure/flow generator is inadequately low, which in turn can be caused by insufficient pressure buildup or low volume states.

While prior art patient monitoring apparatus have reached a high standard in determining parameters characteristic for the contractile capacity of the heart, the cardiac volume status (cardiac preload) is not easily derived from currently available parameters. An increasing body of evidence is suggesting that the conventional intravascular filling pressures measured at different sites (typically central venous pressure (CVP) and pulmonary artery occlusion pressure (PAOP) do not correlate with preload in both pathological and healthy states, as discussed in Marek PE: Assessment of intravascular volume: a comedy of errors, Crit Care Med 2001, 29: 1635-6; Michard F, Teboul J L: Predicting fluid responsiveness in ICU patients: a critical analysis of the evidence, Chest 2002, 121: 2000-8 and Kumar A, Anel R, Bunnell E, et al.: Pulmonary artery occlusion pressure and central venous pressure fail to predict ventricular filling volume, cardiac performance, or the response to volume infusion in normal subjects, Crit Care Med 2004, 32(3):691-9. Volumetric parameters such as left ventricular end-diastolic area (LVEDA), right ventricular end-diastolic volume (RVEDV) and global end-diastolic volume (GEDV) have been proposed as superior indices of preload by Michard F, Teboul J L [see above], Tousignant C P, Walsh F, Mazer C D [The use of transesophageal echocardiography for preload assessment in critically ill patients. Anesth Analg 2000, 90:351-5] and Diebel L N, Wilson R F, Tagett M G, et al. [End-diastolic volume: a better indicator of preload in the critically ill, Arch Surg 1992, 127:817-22]. However, to further complicate matters, the response to volume loading in equal preload conditions will also depend on the underlying myocardial contractility as defined by the slope of the Frank-Starling curve as discussed in Michard F, Reuter D A: Assessing cardiac preload or fluid responsiveness? It depends on the question we want to answer, Intensive Care Med 2003, 29:1396. Specifically in low and high preload states, the concept of "volumerecruitable" cardiac output (CO) will depend more on underlying contractile reserve than on preload, as described by Diebel L N, Wilson R F, Tagett M G, et al. [see above].

Recently, so called dynamic indices of preload such as pulse pressure variation (PPV) and stroke volume variation (SVV) have been advocated by Michard F, Boussat S, Chemla D, et al. [Relation between respiratory changes in arterial pulse pressure and fluid responsiveness in septic patients with acute respiratory failure, Am J Respir Crit Care Med 2000, 162:134-8], Marx G, Cope T, McCrossan L, et al. [Assessing fluid responsiveness by stroke volume variation in mechanically ventilated patients with severe sepsis, Eur J Anaesth 2004, 21:132-8] and Hofer C K, Müller S M, Furrer L, et al. [Stroke volume and pulse pressure variation for prediction of fluid responsiveness in patients undergoing off-pump coronary artery bypass grafting, Chest 2005, 128:848-54] as more reliable indicators of whether a given cardiac output will increase after volume loading, regardless of preload. Patient monitors relying on these indices as indications for a patient's volume responsiveness are also limited, in that they are unreliable in patients in arrhythmia or patients breathing spontaneously.

In view of the above, it is an object of the present invention to provide a patient monitoring apparatus suitable to provide better indication of actual volume responsiveness and thus improve the basis for assessment of hemodynamically critical situations.

According to one aspect of the present invention, this object is accomplished by providing a patient monitoring apparatus according to claim 1. Advantageous embodiments of the present invention can be configured according to any of claims 2-18.

According to another aspect of the present invention, this object is accomplished by providing a method according to claim 19. Further advantageous embodiments of the present invention can be configured according to any of claims 20-35.

It has been found that the novel parameters corrected global enddiastolic volume cGEDV and corrected right ventricular enddiastolic volume cRVEDV determined by a patient monitoring apparatus according to the present invention are parameters very suitable to indicate volume responsiveness and/or preload of a patient. If corrected end-diastolic volumes are low, this is an indication that preload is low and administering blood/fluid may help to stabilize or improve the condition of the monitored patient. If corrected end-diastolic volumes are high, this is an indication that preload is high and administering blood/fluid may not contribute to stabilizing or improving the condition of the monitored patient and thus other therapeutic measures will have to be taken. Changes of these parameters correlate well with cardiac output in that an increase of corrected end-diastolic volumes usually coincides with an increase of cardiac output and a decrease of corrected end-diastolic volumes usually coincides with a decrease of cardiac output.

The inventive patient monitoring apparatus function well with both mechanically ventilated and naturally breathing patients.

Generally, any of the embodiments described or options mentioned herein may be particularly advantageous depending on the actual conditions of application. Further, features of one embodiment may be combined with features of another embodiment as well as features known per se from the prior art as far as technically possible and unless indicated otherwise.

The accompanying drawings, which are schematic illustrations, serve for a better understanding of the features of the present invention. In both drawings, the same reference numerals have been used for corresponding features.

FIG. 1 schematically illustrates an example of a patient monitoring apparatus according to the present invention as part of a system for combined right heart and transpulmonary thermodilution measurements.

Figure 2:
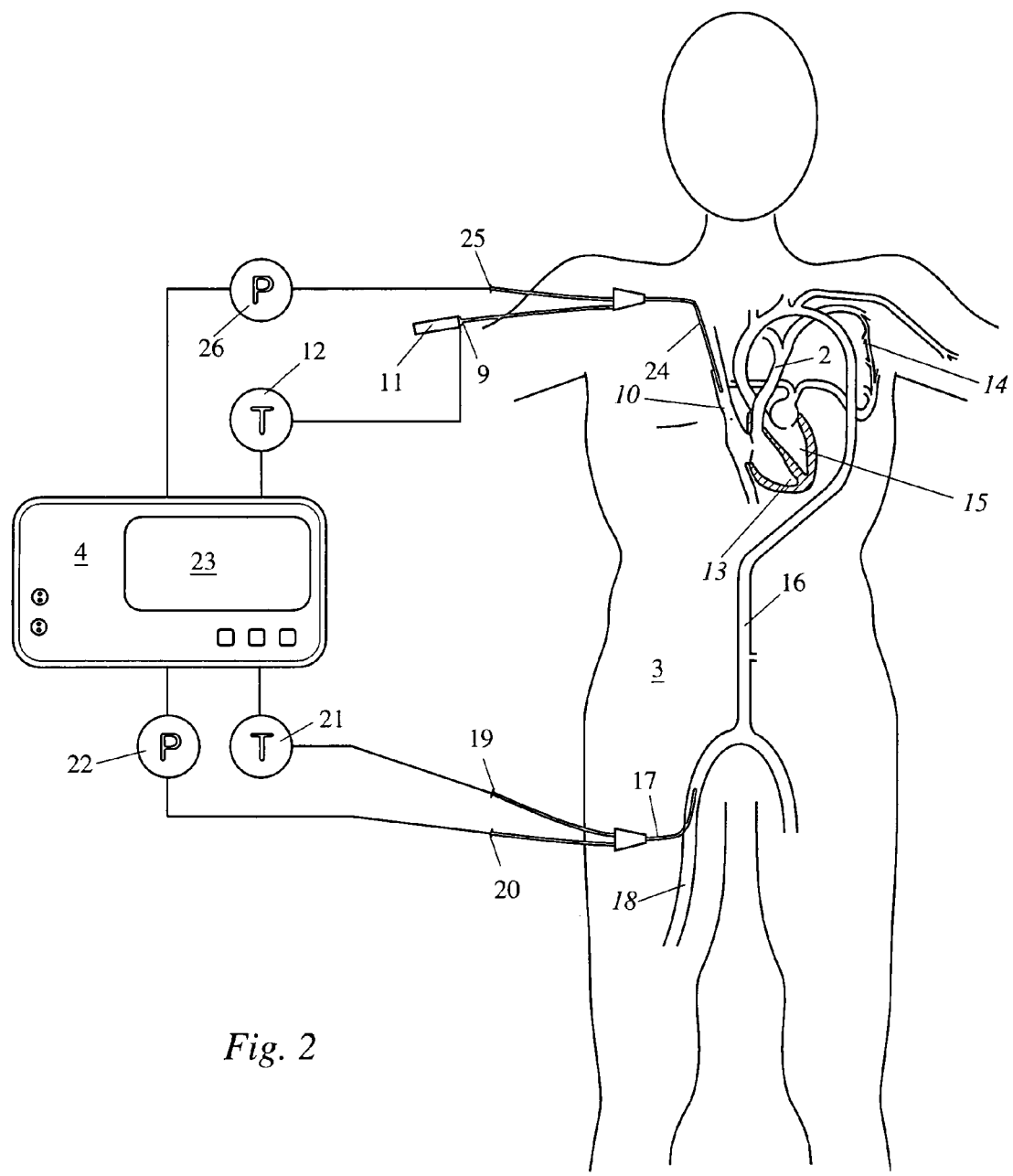

FIG. 2 illustrates, in a manner similar to FIG. 1, a simplified setup with another patient monitoring apparatus according to the present invention as part of a system for transpulmonary thermodilution measurements.

Both systems illustrated in FIGS. 1 and 2 are further equipped for performing pulse contour analysis. Though the first described embodiment is especially preferred, any of the embodiments described or options mentioned herein as well as other embodiments within the scope of the claims may be particularly advantageous depending on the actual conditions of application, as already mentioned above.

FIG. 1 schematically illustrates a system of combined right heart and transpulmonary thermodilution measurements, which comprises a right heart catheter 1 extending into the pulmonary artery 2 of the patient 3 equipped with a distal pressure sensor for measuring blood pressure in the pulmonary artery 2 and a distal temperature sensor for measuring the temperature in the pulmonary artery 2 near the catheter tip. The sensor signals are transmitted to the patient monitor 4 via proximal catheter ports 5, 6 and transducers 7, 8, respectively.

The right heart catheter 1 further comprises another proximal port 9 connected with a lumen, the distal opening of which is located in the central vein (vena cava superior) 10. This lumen is used for injecting a bolus with a temperature different (usually lower) from the patient's blood temperature, thus introducing a travelling temperature deviation to the blood stream. As an alternative, a temperature deviation may be introduced by local heating or cooling in the central vein using a catheter equipped with heating (such as a heating coil) or cooling means (such as a Peltier-element), respectively. A thermodilution setup and a central venous catheter assembly equipped with means for local heating of central venous blood, which can be implemented correspondingly in a right heart catheter 1 assembly as well, are described in EP 1 236 435 A1. Preferably, the proximal port 9 is equipped with an injection channel 11 for accomplishing a bolus injection as well-defined as possible in terms of time and duration of bolus injection as well as bolus temperature. For this, the injection channel 11 may comprise a pressure switch and a temperature sensor connected with the patient monitor 4 via a transducer 12. The injection channel may be configured as described in EP 1 034 737 A1.

The system further comprises an arterial catheter 17 comprising a temperature sensor for measuring the local blood temperature in an artery 18 and a pressure sensor for measuring the arterial blood pressure. Each of the sensors is connected with the patient monitor 4 via proximal catheter ports 19, 20 and transducers 21, 22, respectively. Though the arterial catheter 17 is placed in a femoral artery in the schematic view of FIG. 1, catheter placement in other arteries such as axillary (brachial) artery or radial artery may also be suitable.

Though not described in detail in this application, a setup without the arterial catheter 17 may also be used (for determining the corrected right ventricular end-diastolic volume cREDV as described herein-below).

The temperature deviation introduced to the patient's 3 blood stream by bolus injection or local heating dilutes while travelling through the right heart 13, pulmonary circulation 14, left heart 15 and systemic circulation 16. This dilution is evaluated by applying known thermodilution algorithms using temperature over time measurements performed with the distal temperature sensor of the right heart catheter 1 and the temperature sensor of the arterial catheter 17. The patient monitor 4 is adapted to perform this evaluation using an evaluation program stored in a memory of the patient monitor 4.

In particular, global end-diastolic volume GEDV is determined in the following manner.

$$GEDV = ITTV - PTV$$

wherein ITTV is the intrathoracic thermo volume and PTV is the pulmonary thermo volume.

These parameters are determined as follows $$ITTV = CO \cdot MTt_{TDa}$$

$$PTV = CO \cdot DSt_{TDa}$$

wherein $MTt_{TDa}$ is the mean transit time and $DSt_{TDa}$ is the downslope time (i.e. the time the blood temperature difference $\Delta T_B(t)$ takes to drop by the factor 1/e where the dilution curve shows exponential decay) both determined from the dilution curve measured by the transpulmonary setup. CO is the cardiac output and may be determined either by pulse contour analysis using known algorithms (such as disclosed in U.S. Pat. No. 6,315,735) based on the pressure-over-time signal measured with the pressure sensor of the arterial catheter 17 or the catheter 1, or it may be determined (using the temperature-over-time signal measured with the temperature sensor of the arterial catheter 17 or the catheter 1) by known thermodilution algorithms based on the Stewart-Hamilton equation $$CO = \frac{V_L(T_B - T_L)K_1 K_2}{\int_\Delta T_B(t)dt}$$

wherein $T_B$ is the initial blood temperature, $T_L$ is the temperature of the liquid bolus, which is used as thermal indicator, $V_L$ is the thermal indicator volume, $K_1$ and $K_2$ are constants to consider the specific measurement setup, and $\Delta T_B(t)$ is the blood temperature as a function of time with respect to the baseline blood temperature $T_B$.

Thus, global end-diastolic volume GEDV is determined as $$GEDV = CO \cdot (MTtTDa - DstTDa)$$

The patient monitor 4 also determines global ejection fraction GEF according to $$GEF = 4 \cdot SV/GEDV$$

wherein SV is the stroke volume which is determined according to $$SV = CO/HR$$

wherein HR is the patient's 3 heart rate.

From the global end-diastolic volume GEDV and the global ejection fraction GEF the patient monitor 4 determines a corrected global end-diastolic volume cGEDV according to $$cGEDV = GEDV/f(GEF)$$

which is used as a novel parameter for volume responsiveness of the patient 3 as set forth herein-below. In the above formula, $f(GEF)$ is a correction function depending on global ejection fraction GEF which preferably is of the form $$f(GEF) = \exp(k1 \cdot (k2 - GEF))$$

wherein k1 and k2 are constants of which k2 represents a normal global ejection fraction which has been determined as an average value of the ejection fractions of a plurality of persons and may range between 0 and 1, usually 0.35-0.45, preferably 0.4. The constant k1 has been empirically determined to be approximately 2.74 but may be adapted depending on additional empirical data.

In addition (or alternatively) right ventricular end-diastolic volume the patient monitor 4 determines RVEDV as $$RVEDV = COpa \cdot DStTDpa$$

wherein DStTDpa is the downslope time (i.e. the time the blood temperature difference $\Delta TB(t)$ takes to drop by the factor 1/e where the dilution curve shows exponential decay) determined from the dilution curve measured in the pulmonary artery 2 by the right heart setup. COpa is the cardiac output measured in the pulmonary artery 2 by the right heart setup and may be determined either by pulse contour analysis using known algorithms (based on the pressure-over-time signal measured with the pressure sensor of the right heart catheter 1), or it may be determined by known thermodilution algorithms (based on the temperature-over-time signal measured with the temperature sensor of the right heart catheter 1).

The patient monitor 4 also determines right ventricular ejection fraction RVEF according to $$RVEF = SV_{pa}/RVEDV$$

wherein $SV_{pa}$ is the stroke volume determined by the right heart setup according to $$SV_{pa} = CO_{pa}/HR$$

wherein HR is the patient's 3 heart rate.

From the right ventricular end-diastolic volume RVEDV and the right ventricular ejection fraction RVEF the patient monitor 4 determines a corrected right ventricular end-diastolic volume cRVEDV according to $$cRVEDV = RVEDV/f(RVEF)$$

which is used as a novel parameter for volume responsiveness of the patient 3 as set forth herein-below. In the above formula, $f(RVEF)$ is a correction function depending on right ventricular ejection fraction RVEF which preferably is of the form $$f(RVEV) = \exp(k3 \cdot (k4 - RVEF))$$

wherein k3 and k4 are constants of which k4 represents a normal right ventricular ejection fraction which has been determined as an average value of the ejection fractions of a plurality of persons and may range between 0 and 1, usually 0.45-0.55, preferably 0.5. The constant k3 has been empirically determined to be approximately 2.74 but may be adapted depending on additional empirical data.

Corrected global end-diastolic volume cGEDV and corrected right ventricular end-diastolic volume cRVEDV determined by the patient monitor 4 are parameters very suitable to indicate volume responsiveness and/or preload of a patient 3. If corrected end-diastolic volumes are low, this is an indication that preload is low and administering blood/fluid may help to stabilize or improve the condition of the monitored patient 3. If corrected end-diastolic volumes are high, this is an indication that preload is high and administering blood/fluid may not contribute to stabilizing or improving the condition of the monitored patient 3 and thus other therapeutic measures will have to be taken. Changes of these parameters correlate well with cardiac output in that an increase of corrected end-diastolic volumes usually coincides with an increase of cardiac output and a decrease of corrected end-diastolic volumes usually coincides with a decrease of cardiac output.

Determined parameters are displayed as numerical values and/or in charts and/or presented in graphical manner on the display 23 which also serves to guide operation.

To improve handling, the patient monitor 4 comprises a memory to store previously corrected end-diastolic volumes cGEDV and/or cRVEDV and a software function is implemented to determine the difference $\Delta$cGEDV and/or $\Delta$cRVEDV between instant corrected end-diastolic volumes cGEDV and/or cRVEDV and corrected end-diastolic volumes cGEDV and/or cRVEDV, respectively, determined a predetermined time span earlier than determination of the instant corrected end-diastolic volumes. Further, the patient monitor 4 has stored a database including data sets, each of which includes a value range of the end-diastolic volume difference $\Delta$cGEDV and/or $\Delta$cRVEDV, respectively, and a counter measure recommendation corresponding to said value range of the respective end-diastolic volume difference. An audible and/or visible alarm is emitted if the determined corrected end-diastolic volume cGEDV or cRVEDV and/or the determined difference between an instant corrected end-diastolic volume cGEDV or cRVEDV and a respective corrected end-diastolic volume determined a predetermined time span earlier than determination of the instant corrected end-diastolic volume cGEDV or cRVEDV exceeds or becomes smaller than a respective upper or lower threshold value. The threshold values and database sets mentioned above have previously been stored on the basis of scientific data acquired by experienced physicians so that the staff operating the inventive patient monitor 4 can benefit from the knowledge of experienced experts.

As advantageous options, additional functions may be implemented in the patient monitor 4. The various database and alarm functions may be enhanced using internal decision trees similar to expert systems. Further (especially in connection with display, documentation, database and alarm functions) various conditions of the instant application may be considered which can be input in an input screen mask displayed on display 23. These conditions can include but are not limited to the following: Is the patient 3 mechanically ventilated? Does the patient 3 have a valvolopathy? Does the patient have a dilated cardiomyopathy (CMP)? Does the patient 3 suffer from an abdominal aneurysm?

Among advantageous evaluation options, the following may also be implemented, which involve consideration of relations between various determined parameters. If a low global injection fraction GEF has been determined in the respective step described above, the patient monitor 4 can perform an assessment, whether the corrected global enddiastolic volume cGEDV is high or low (by comparing the determined corrected global end-diastolic volume cGEDV with stored threshold values). If cGEDV is high, it is indicated on the display 23 that the patient may either have a dilated CMP with pump failure or there may be an overestimation of determined volumes. If cGEDV low, it is indicated that there is a preload insufficiency.

Further, as pulse contour analysis algorithms are also implemented, a function may be implemented for assessing whether there is a discrepancy between preload/volume responsiveness determined on the basis of stroke volume variation SVV/pulse pressure variation PPV and preload/volume responsiveness determined on the basis of corrected end-diastolic volumes.

The system illustrated in FIG. 2 is similar to the system in FIG. 1, however, no right heart catheter but a central venous catheter 24 is applied. Use of a a central venous catheter 24 is less invasive than use of a right heart catheter 1, but the parameters RVEDV, $CO_{pa}$, $DSt_{TDpa}$, $SV_{pa}$, RVEF and thus cRVEDV and ΔcRVEDV cannot be determined as described above.

The central venous catheter 24 is equipped with an ejection channel 11 for injecting a bolus into the central vein 10. Further, the central venous catheter 24 comprises a pressure sensor for measuring central venous pressure, which is optional. The respective sensor signal is transmitted via catheter port 25 and transducer 26 to the patient monitor 4.

Transpulmonary thermodilution measurements, using the arterial catheter 17, and evaluation thereof are conducted as described above in connection with FIG. 1, and—subject to the limitations mentioned above—the same display, database and alarm functions may be implemented as described above.

What is claimed is:

1. A patient monitoring apparatus for determining at least one of volume responsiveness and cardiac preload of a monitored patient, said apparatus comprising
   a thermodilution measurement assembly for inducing a local temperature change at a first location of the patient's circulatory system and measuring a response signal downstream of said first location and
   an evaluation unit adapted to determine an end-diastolic volume EDV from said measured response signal
      wherein said evaluation unit is further adapted to determine, as a parameter for at least one of volume responsiveness and cardiac preload, a corrected end-diastolic volume cEDV as the quotient of said end-diastolic volume EDV and a function $f$ of an ejection fraction EF of said patient according to the formula $cEDV=EDV/f(EF)$.

2. A patient monitoring apparatus according to claim 1, wherein said function $f$ is an exponential function.

3. A patient monitoring apparatus according to claim 2, wherein said function $f$ is of the type $f=\exp(k1\cdot(k2-EF))$ wherein k1 is a first constant and k2 is a second constant.

4. A patient monitoring apparatus according to claim 3, wherein said first constant k1 is positive.

5. A patient monitoring apparatus according to claim 4, wherein said first constant k1 is between 2.5 and 3.

6. A patient monitoring apparatus according to claim 3, wherein said second constant k2 represents a normal ejection fraction which has been determined as an average value of the ejection fractions of a plurality of persons.

7. A patient monitoring apparatus according to claim 1, wherein said thermodilution measurement assembly includes injection means (11) for central venous injection of a bolus with a temperature deviating from the patient's blood temperature.

8. A patient monitoring apparatus according to claim 1, wherein said thermodilution measurement assembly includes heating means for locally influencing the patient's blood temperature in a central vein.

9. A patient monitoring apparatus according to claim 1, wherein said thermodilution measurement assembly includes cooling means for locally influencing the patient's blood temperature in a central vein.

10. A patient monitoring apparatus according to claim 1, wherein said thermodilution measurement assembly includes a right heart catheter with sensor means for measuring said response signal in the pulmonary artery of the patient
   and wherein said end-diastolic volume EDV is a right ventricular end-diastolic volume RVEDV, said ejection fraction EF is a right ventricular ejection fraction RVEF and said evaluation unit is adapted to determine a corrected right ventricular end-diastolic volume cRVEDV according to the formula $cRVEDV=RVEDV/f(RVEF)$.

11. A patient monitoring apparatus according to claim 10, wherein said function $f$ is of the type $f=\exp(k1\cdot(k2-RVEF))$ and wherein k1 is a first constant and k2 is a second constant which is between 0 and 1.

12. A patient monitoring apparatus according to claim 1, wherein said thermodilution measurement assembly includes an arterial catheter with sensor means for measuring said response signal in an artery of the patient
   and wherein said end-diastolic volume EDV is a global end-diastolic volume GEDV, said ejection fraction EF is a global ejection fraction GEF and said evaluation unit is adapted to determine a corrected global enddiastolic volume cGEDV according to the formula $cGEDV=GEDV/f(GEF)$.

13. A patient monitoring apparatus according to claim 12, wherein said function $f$ is of the type $f=\exp(k1\cdot(k2-GEF))$ and wherein k1 is a first constant and k2 is a second constant which is between 0 and 1.

14. A patient monitoring apparatus according to claim 1, wherein said evaluation unit includes means to store previously corrected end-diastolic volumes cEDV and is further adapted to determine a difference ΔcEDV between an instant corrected end-diastolic volume cEDV and a corrected end-diastolic volume determined a predetermined time span earlier than determination of the instant corrected end-diastolic volume.

15. A patient monitoring apparatus according to claim 14, wherein said evaluation unit includes database means storing data sets, each of the data sets including a value range of the end-diastolic volume difference ΔcEDV and a counter measure recommendation corresponding to said value range of the end-diastolic volume difference ΔcEDV.

16. A patient monitoring apparatus according to claim 1, wherein said monitoring apparatus comprises alarm means for emitting at least one of an audible alarm and a visible alarm if at least one of the determined corrected end-diastolic volume cEDV and the determined difference ΔcEDV between the instant corrected end-diastolic volume cEDV and a corrected end-diastolic volume determined a predetermined time span earlier than determination of the instant corrected end-diastolic volume is outside a range defined by at least one of an upper threshold value and a lower threshold value.

17. A patient monitoring apparatus according to claim 1, wherein said monitoring apparatus further comprises a central venous pressure measurement assembly.

18. A patient monitoring apparatus according to claim 1, wherein said monitoring apparatus further comprises an arterial pressure measurement assembly and said evaluation unit is further adapted to read in arterial pressure readings from said arterial pressure measurement assembly and to calculate hemodynamic parameters on the basis of said arterial pressure readings using pulse contour algorithms.

19. A method for determining at least one of volume responsiveness and cardiac preload of a monitored patient, said method comprising the steps of
inducing a local temperature change at a first location of the patient's circulatory system,
measuring a response signal downstream of said first location
determining in an evaluation unit an end-diastolic volume EDV from said measured response signal, and
determining in an evaluation unit, as a parameter for at least one of volume responsiveness and cardiac preload, a corrected end-diastolic volume cEDV as the quotient of said end-diastolic volume EDV and a function $f$ of an ejection fraction EF of said patient according to the formula $cEDV=EDV/f(EF)$.

20. A method according to claim 19, wherein said function $f$ is an exponential function.

21. A method according to claim 20, wherein said function $f$ is of the type $f=\exp(k1 \cdot (k2-EF))$ wherein k1 is a first constant and k2 is a second constant.

22. A method according to claim 21, wherein said first constant k1 is positive.

23. A method according to claim 22, wherein said first constant k1 is between 2.5 and 3.

24. A method according to claim 21, wherein said second constant k2 represents a normal ejection fraction which has been determined as an average value of the ejection fractions of a plurality of persons.

25. A method according to claim 19, wherein said step of inducing a local temperature change includes injection of a bolus with a temperature deviating from the patient's blood temperature.

26. A method according to claim 19, wherein said step of inducing a local temperature change includes locally heating the patient's blood in a central vein.

27. A method according to claim 19, wherein said step of inducing a local temperature change includes locally cooling the patient's blood in a central vein.

28. A method according to claim 19, wherein said step of measuring a response signal includes measuring said response signal in the pulmonary artery of the patient using a right heart catheter,
and wherein said end-diastolic volume EDV is a right ventricular end-diastolic volume RVEDV, said ejection fraction EF is a right ventricular ejection fraction RVEF and a corrected right ventricular end-diastolic volume cRVEDV is determined according to the formula $cRVEDV=RVEDV/f(RVEF)$.

29. A method according to claim 28, wherein said function $f$ is of the type $f=\exp(k1 \cdot (k2-RVEF))$ and wherein k1 is a first constant and k2 is a second constant which is between 0 and 1.

30. A method according to claim 19, wherein said step of measuring a response signal includes measuring said response signal in an artery of the patient
and wherein said end-diastolic volume EDV is a global end-diastolic volume GEDV, said ejection fraction EF is a global ejection fraction GEF and a corrected global end-diastolic volume cGEDV is determined according to the formula $cGEDV=GEDV/f(GEF)$.

31. A method according to claim 30, wherein said function $f$ is of the type $f=\exp(k1 \cdot (k2-GEF))$ and wherein k1 is a first constant and k2 is a second constant which is between 0 and 1.

32. A method according to claim 19, wherein previously corrected end-diastolic volumes cEDV are stored and a difference ΔcEDV is determined between an instant corrected end-diastolic volume cEDV and a corrected end-diastolic volume determined a predetermined time span earlier than determination of the instant corrected end-diastolic volume.

33. A method according to claim 32, wherein data sets are stored, each of the data sets including a value range of the end-diastolic volume difference ΔcEDV and a counter measure recommendation corresponding to said value range of the end-diastolic volume difference ΔcEDV.

34. A method according to claim 19, wherein at least one of an audible alarm and a visible alarm are emitted if at least one of the determined corrected end-diastolic volume cEDV and the determined difference ΔcEDV between the instant corrected end-diastolic volume cEDV and a corrected end-diastolic volume determined a predetermined time span earlier than determination of the instant corrected end-diastolic volume is outside a range defined by at least one of an upper threshold value and a lower threshold value.

35. A method according to claim 19, wherein arterial pressure is measured and hemodynamic parameters determines on the basis of arterial pressure readings using pulse contour algorithms.

* * * * *